United States Patent [19]

Jordan et al.

[11] Patent Number: 5,777,120
[45] Date of Patent: Jul. 7, 1998

[54] CATIONIC ALUMINUM ALKYL COMPLEXES INCORPORATING AMIDINATE LIGANDS AS POLYMERIZATION CATALYSTS

[75] Inventors: Richard F. Jordan; Martyn P. Coles, both of Iowa City, Iowa

[73] Assignee: University of Iowa Research Foundation, Iowa City, Iowa

[21] Appl. No.: 818,297

[22] Filed: Mar. 14, 1997

[51] Int. Cl.$^6$ ............................ C07F 7/02; C07F 5/06; C07F 9/02; C07D 305/00
[52] U.S. Cl. ............................ 546/2; 546/6; 549/210; 556/172; 556/173; 556/174; 556/175; 556/176; 556/187; 526/189; 526/204; 526/217; 502/150; 502/152; 502/167; 502/200
[58] Field of Search ............................ 546/2, 6; 549/210; 556/172, 173, 174, 175, 176, 187; 502/150, 152, 167, 200

[56] References Cited

U.S. PATENT DOCUMENTS

| | | | |
|---|---|---|---|
| 2,699,457 | 1/1955 | Ziegler et al. | 556/176 |
| 3,373,178 | 3/1968 | Schmidt et al. | 556/173 |
| 3,644,224 | 2/1972 | Hani et al. | 260/2 A |
| 4,176,090 | 11/1979 | Vaughan et al. | 252/445 Z |
| 4,325,885 | 4/1982 | Dozzi et al. | 260/448 R |
| 4,434,103 | 2/1984 | Interrante | 260/448 B |
| 5,066,741 | 11/1991 | Campbell, Jr. | 526/171 |
| 5,235,078 | 8/1993 | Pohl et al. | 556/1 |
| 5,318,935 | 6/1994 | Canich et al. | 502/117 |
| 5,371,309 | 12/1994 | Moini | 585/407 |
| 5,428,120 | 6/1995 | Newman et al. | 526/160 |
| 5,453,410 | 9/1995 | Kolthammer et al. | 502/155 |
| 5,468,707 | 11/1995 | Pohl et al. | 502/153 |
| 5,502,128 | 3/1996 | Flores et al. | 526/160 |
| 5,527,752 | 6/1996 | Reichle et al. | 502/117 |
| 5,561,216 | 10/1996 | Barborak et al. | 528/392 |
| 5,707,913 | 1/1998 | Schlund et al. | 502/200 |

FOREIGN PATENT DOCUMENTS

| | | |
|---|---|---|
| 0 493 995 A1 | 7/1992 | European Pat. Off. . |
| 220 029 | 3/1985 | German Dem. Rep. ............ 556/175 |

OTHER PUBLICATIONS

H. Schmidbaur et al., Angew. Chem. Int. Ed. Eng., vol. 4, no. 10, p. 877, 1965.

K. Dehnicke et al., J. Organomet. Chem., vol. 352, pp. C1–C4, 1988.

M. Wedler et al., J. Organomet. Chem., vol. 388, pp. 21–45, 1990.

K. Dehnicke, Chemiker–Zeitung, vol. 114, No. 10, pp. 295–304, Oct. 1990.

J. Buijink et al., Z. Naturforsch., vol. 46b, pp. 1328–1332, 1991.

A. Chernega et al., J. Chem. Soc., Chem. Commun., pp. 1415–1417, 1993.

R. Duchateau et al., J. Am. Chem. Soc., vol. 115, pp. 4931–4932, 1993.

A. Goodwin et al., Macromolecules, vol. 27, pp. 5520–5522, 1994.

R. Gomez et al., J. Organomet. Chem., vol. 491, pp. 153–158, 1995.

Chemical Abstracts; vol. 118, p. 18, 1993, 169853w, Pons, et al., *Crosslinked poly(organosilylhydrazine) ceramic* . . . .

Chemical Abstracts, vol. 123, p. 7, 1995, 84111f, Atwood, et al., *Cationic Aluminum Compounds* . . . .

*Primary Examiner*—Glenn Caldarola
*Assistant Examiner*—J. Pasterczyk
*Attorney, Agent, or Firm*—Zarley, McKee, Thomte, Voorhees, & Sease

[57] ABSTRACT

Aluminum amidinate compounds of the formula

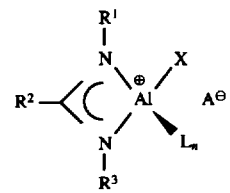

wherein R, R$^2$, and R$^3$ are selected from the group consisting of C$_1$ to C$_{50}$ alkyl, aryl, and silyl groups, X is an anionic ligand, preferably a hydrocarbyl, n=0 or 1, L, if present, is a labile Lewis base ligand, preferably having an oxygen, nitrogen, or phosphorus atom donating a lone pair of electrons to the aluminum center, and A$^-$ is an anion which balances the charge of the aluminum cation and only weakly if at all coordinates to the aluminum center and preferably contains boron, are disclosed. These compounds are useful as olefin polymerization catalysts without the need for cocatalysts or transition metal species.

8 Claims, No Drawings

CATIONIC ALUMINUM ALKYL COMPLEXES INCORPORATING AMIDINATE LIGANDS AS POLYMERIZATION CATALYSTS

BACKGROUND OF THE INVENTION

Ziegler-Natta type catalysts for polymerization of unsaturated hydrocarbons, such as alpha olefins, have long been the state of the art catalysts for such reactions. Typically, Ziegler-Natta type catalysts are composed of transition metal salts and aluminum alkyl compounds. While these catalysts are very effective and have a long-established record of use, they are not without drawbacks. For example, transition metals are expensive, potentially present some toxicity hazards, and to some are environmentally objectionable. Therefore, continuing efforts towards development of other suitable olefin polymerization catalysts have occurred. For example, metallocene catalysts have been developed for use in alpha olefin polymerization.

This invention has as its primary objective the development of catalysts for polymerization of unsaturated hydrocarbons which successfully polymerize without a transition metal moiety as part of the catalyst.

Another objective of the present invention is to prepare such catalysts in high yields and by use of convenient and practical synthetic methods.

A yet further objective of the present invention is a method of polymerizing unsaturated hydrocarbons using Ziegler-Natta like catalysts in the sense that the catalyst behaves similarly to Ziegler-Natta catalysts, but yet avoids the use of transition metals.

The method and manner of accomplishing each of the above objectives, as well as others, will become apparent from the detailed description of the invention which follows hereinafter.

SUMMARY OF THE INVENTION

The invention relates to novel catalysts, processes of synthesizing the catalysts, and to olefin polymerization reactions using the catalysts. The catalysts are cationic aluminum amidinate compounds. These compounds behave similarly to Ziegler-Natta catalysts, but avoid the use of transition metals.

DETAILED DESCRIPTION OF THE INVENTION

The formation of polyethylene from the reaction of neutral aluminum compounds including $Cl_2AlCH(Me)AlCl_2$ or $(AlR_3)_2$ with ethylene in the temperature range 25 to 50° C. has been reported in Martin, H.; Bretinger, H. *Makromol. Chem.* 1992, 193, 1283. However, the reported catalytic activities are very low (1.6 ×10$^{-1}$ –3.8 ×10$^{-4}$ g PE/(mol*h*atm)).

After extensive work with transition metal catalysts and investigation into the polymerization of unsaturated hydrocarbons such as olefins with a view to improving on the conventional processes by eliminating transition elements, a process has been discovered for polymerizing such unsaturated hydrocarbons with an entirely new class of catalyst compounds.

The catalysts are cationic aluminum amidinate compounds of the following formula:

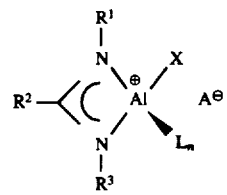

wherein $R^1$, $R^2$ and $R^3$ are selected from the group consisting of $C_1$ to $C_{50}$ alkyl, aryl, or silyl groups, X is an anionic ligand, n=0 or 1, L is a labile Lewis base or donor ligand or a neutral aluminum species capable of coordination, and $A^-$ is a counterbalancing non-coordinating or weakly coordinating anion.

The amidinate ligands (in anionic form) may be represented by structure C, which is the resonance hybrid of localized resonance structures A and B. Similarly, the base-free cationic aluminum complexes (n=b 0) may be represented by structure F, which is the resonance hybrid of localized resonance structures D and E. The situation for the base-stabilized cationic aluminum complexes (n=1) is analogous.

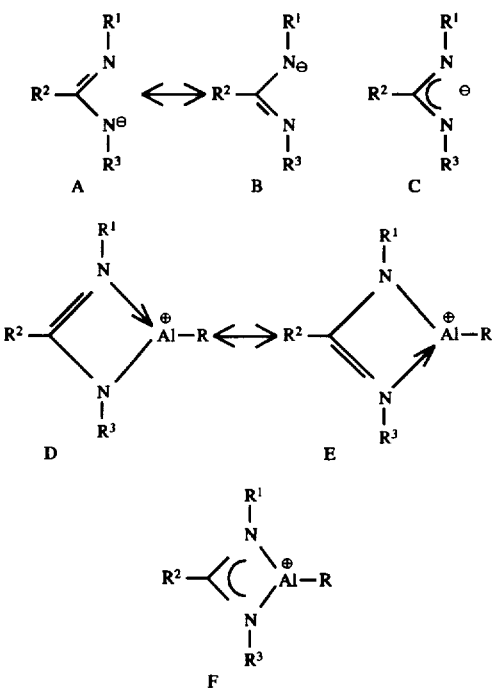

In the above description of the resonance structures, $R^1$, $R^2$ and $R^3$ are as earlier described. With regard to the invention, while they broadly can be $C_1$ to $C_{50}$, generally speaking, preferred $R^1$, $R^2$ and $R^3$ groups are $C_1$ to $C_{12}$ alkyl, aryl or silyl.

The X moiety can represent a hydride radical, a dialkylamido radical, an alkoxide radical, an aryloxide radical, a hydrocarbyl radical, a substituted hydrocarbyl radical, a halocarbyl radical, or a thiolate radical. L is, of course, labile and can be displaced by other Lewis bases or donor ligands, including olefins, di-olefins, or any other unsaturated monomer.

The $A^-$ moiety represents the non-coordinating or weakly coordinating counterbalancing anion. In particular, it represents a compatible, non-coordinating anion containing a single coordination complex comprising a charge-bearing metal or metalloid core which is relatively large (bulky), capable of stabilizing the active catalyst species and being sufficiently labile to be displaced by olefinic, di-olefinic or acetylenically unsaturated substrates, or other neutral Lewis bases or donor groups, such as ethers, nitrites and the like. Polyhedral borane anions, carborane anions and metallocarborane anions are also useful non-coordinating or weakly coordinating counterbalancing anions.

The key to proper anion design requires that the anionic complex is labile and stable toward reactions in the final catalyst species. Anions which are stable toward reactions with water or Bronsted acids and which do not have acidic protons located on the exterior of the anion (i.e. anionic complexes which do not react with strong acids or bases) possess the stability necessary to qualify as a stable anion for the catalyst system. The properties of the anion which are important for maximum lability include overall size, and shape (i.e. large radius of curvature), and nucleophilicity.

Using these guidelines one can use the chemical literature to choose non-coordinating anions which can serve as components in the catalyst system. In general, suitable anions for the second component may be any stable and bulky anionic complex having the following molecular attributes: 1) the anion should have a molecular diameter about or greater than 4 angstroms; 2) the anion should form stable salts with reducible Lewis Acids and protonated Lewis bases; 3) the negative charge on the anion should be delocalized over the framework of the anion or be localized within the core of the anion; 4) the anion should be a relatively poor nucleophile; and 5) the anion should not be a powerful reducing or oxidizing agent. Anions meeting these criteria—such as polynuclear boranes, carboranes, metallacarboranes, polyoxoanions and anionic coordination complexes are well described in the chemical literature.

Illustrative, but not limiting examples of non-coordinating or weakly coordinating counterbalancing anions are tetra (phenyl)borate, tetra(p-tolyl)borate, tetra (pentafluorophenyl)borate, tetra (3,5-bis-trifluoromethylphenyl)borate, (methyl)tris(pentafluorophenyl)borate, $C_2B_9H_{12}^-$, $CB_{11}H_{12}^-$, $B_{12}H_{12}^{2-}$, and $(C_2B_9H_{11})_2Co^-$.

As earlier stated, generally, these anions are (1) labile and can be displaced by an olefin, di-olefin or acetylenically unsaturated monomer, have a molecular diameter about or greater than 4 angstroms, form stable salts with reducible Lewis acids and protonated Lewis bases, have a negative charge delocalized over the framework on the anion of which the core thereof is not a reducing or oxidizing agent, and are relatively poor nucleophiles. For other examples of such counterbalancing, non-coordinating or weakly coordinating anions, see Strauss, S. H.; Chemical Reviews, 1993, 93, 927–942.

L, the optional labile Lewis base ligand, is also conventional and well known. It can, for example, be represented by tetrahydrofuran, ethers such as dimethyl ether, amines, alkyl amines, pyridine, substituted pyridines, and phosphines. L may also be represented by a neutral aluminum species which coordinates to the cation through a bridging group, such as $\{MeC(NPr^i)_2\}AlMe_2;AlMe_3$; and $AlCl_3$. The presence of such neutral coordinating ligands L is not critical, and they may or may not be present as deemed appropriate in any particular reaction.

The cationic aluminum amidinate complexes may be prepared by reacting a neutral precursor complex of the type $\{R^2C(NR^1)(NR^3)\}AlX_2$, where $R^1$, $R^2$, $R^3$, and X are as defined above, with an activator compound which is capable of abstracting one X⁻group from the precursor complex or of cleaving one Al—X bond of the precursor complex. Suitable activator compounds include Bronsted acids, such as ammonium salts, Lewis acids, such as $AlCl_3$ and $B(C_6F_5)_3$, ionic reagents such as $Ag^+$and trityl salts, and oxidizing agents such as ferrocenium salts. Illustrative, but not limiting examples of suitable activator compounds are N,N-dimethylanilinium tetra(pentafluorophenyl)borate, methyldiphenylammonium tetra(pentafluorophenyl)borate, aluminum trichloride, tris(pentafluorophenyl)boron, silver (I) tetra(phenyl)borate, triphenylcarbenium tetra (pentafluorophenyl)borate, and ferrocenium tetra(phenyl) borate.

The synthesis of the catalyst compounds as earlier described for the present invention is particularly straightforward. Ideally, they are prepared on a high vacuum line under an inert atmosphere in the presence of solvents in the manner illustrated in the examples below. These examples of synthesis are illustrative and not intended to be limiting of the invention.

All manipulations were performed on a high-vacuum line or in a glove box under a purified $N_2$ atmosphere. Solvents were distilled from Na/benzophenone ketyl, except for chlorinated solvents, which were distilled from activated molecular sieves (3 Å) or $P_2O_5$.

NMR spectra were recorded on a Bruker AMX 360 spectrometer in sealed or Teflon-valved tubes at ambient probe temperature unless otherwise indicated. $^1H$ and $^{13}C$ chemical shifts are reported versus $SiMe_4$ and were determined by reference to the residual $^1H$ and $^{13}C$ solvent peaks. All coupling constants are reported in Hz. The NMR spectra of cationic complexes contained resonances for $B(C_6F_5)_4^-$or $[B(C_6F_5)_3Me]^-$.

NMR data for $B(C_6F_5)_4^-$: $^{13}C$ NMR $(CD_2Cl_2)$: δ 148.6 (d.$^1J_{CF}$=240.0 Hz), 138.7 (d.$^1J_{CF}$=245.4 Hz), 136.8 (d.$^1J_{CF}$= 245.4 Hz), 124.7 (br s, ipso-Ph). NMR data for $MeB(C_6F_5)_3^-$: $^1H$ NMR $(CD_2Cl_2)$: δ 0.47 (br s, 3H, B—$CH_3$). $^{13}C$ NMR $(CD_2Cl_2)$: δ 148.6 (d, $^1J_{CF}$=235.5 Hz), 137.9 (d.$^1J_{CF}$= 242.7 Hz), 136.8 (d.$^1J_{CF}$=246.4 Hz), 129.7 (br s, ipso-Ph), 10.34 (br s, B—$CH_3$).

Mass spectra were obtained using the Direct Insertion Probe (DIP) method, on a VG Analytical Trio I instrument operating at 70 eV. Elemental analyses were performed by Desert Analytics Laboratory.

EXAMPLE 1

($\{MeC(NPr^i)_2\}AlMe_2$)

A solution of 1,3-diisopropylcarbodimide (2.00 g, 10.7 mmol) in hexane (25 mL) was added dropwise via pipette to a rapidly stirred solution of $AlMe_3$ (1.06 mL, 11.0 mmol) in hexane (10 mL). An exothermic reaction was observed. The reaction mixture was stirred at room temperature for 18 h, after which time the volatiles were removed under vacuum affording pure $\{MeC(NPr^i)_2\}AlMe_2$ as a pale yellow liquid (2.30 g, 71%). $^1H$ NMR $(CD_2Cl_2)$: δ 3.50 (sept.$^3J_{HH}$=6.3Hz, 2H, $CHMe_2$), 1.94 (s, 3H, CMe), 1.05 (d.$^3J_{HH}$=6.1 Hz, 12H, $CHMe_2$), −0.82 (s, 6H, $AlMe_2$). $^{13}C$ NMR $(CD_2Cl_2)$: δ 172.5 (s, CMe), 45.3 (d.$^1J_{CH}$=132.2 Hz, $CHMe_2$), 25.3 (q, $^1J_{CH}$=125.6 Hz, $CHMe_2$), 11.1 (q.$^1J_{CH}$=128.3 Hz, CMe),− 9.94 (br q), $^1J_{CH}$=114.1 Hz, $AlMe_2$). Anal. Calcd for $C_{10}H_{23}N_2Al$: C, 60.57; H, 11.69; N, 14.13. Found: C, 60.41; H, 11.96; N, 14.50.

EXAMPLE 2

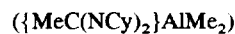
($\{MeC(NCy)_2\}AlMe_2$)

A solution of 1,3-dicyclohexylcarbodiimide (5.00 g, 24.2 mmol) in hexane (40 mL) was added slowly to a solution of AlMe$_3$(2.40 mL, 25.0 mmol) in hexane (15 mL). The solution was stirred for 15 h and the volatiles were removed under vacuum yielding a pale yellow liquid that crystallized upon standing to afford pure {MeC(NCy)$_2$}AlMe$_2$ as off-white crystals. (6.49 g, 93%). $^1$H NMR (CD$_2$Cl$_2$): δ 3.10 (m, 2H, Cy), 1.92 (s, 3H, CMe), 1.69 (m,8H,Cy),1.56(m,2H, Cy), 1.35–1.06(m,8H+2H,Cy),-0.82(s,6H,AlMe$_2$). $^{13}$C NMR (CD$_2$Cl$_2$): δ 172.4(s,CMe), 53.0(d,$^1J_{CH}$=131.4 Hz,Cy-C$_1$), 36.0(t,$^1J_{CH}$=126.5 Hz,Cy), 26.1 (t,$^1J_{CH}$=125.8 Hz,Cy), 25.4 (t,$^1J_{CH}$=126.9 Hz,Cy), 11.2 (q,$^1J_{CH}$=128.0 Hz, CMe),–9.78 (br q),$^1J_{CH}$=112.6 Hz, AlMe$_2$). Anal. Calcd for C$_{16}$H$_{31}$N$_2$Al: C, 69.02; H, 11.22; N, 10.06. Found: C, 68.88; H, 10.44; N, 10.15. Mass Spec. (EI, m/z): 263 |M|$^+$.

EXAMPLE 3

(Li|Bu$^t$C(NPr$^i$)$_2$|)

A solution of 1,3-diisopropylcarbodiimide (5.00 g, 39.6 mmol) in Et$_2$O (50 mL) was cooled to 0° C. Bu$^t$Li(23.30 mL of a 1.7 M solution in pentane, 39.6 mmol) was added dropwise via syringe and the mixture was allowed to warm to room temperature. After 30 min the solvent was removed under vacuum affording a yellow oily solid which was dried under vacuum (18 h, 23° C.) to give a pale yellow solid. Trituration with hexane gave Li[Bu$^t$C(NPr$^i$)$_2$] as an off-white powder (4.56 g, 61%). $^1$H NMR (THF-d$_8$): δ 3.84 (sept, $^3J_{HH}$=5.7 Hz, 2H, CHMe$_2$), 1.13 (s, 9H, CMe$_3$), 0.96 (d, $^3J_{HH}$=6.1 Hz, 12H, CHMe$_2$). $^{13}$C NMR (THF-d$_8$): δ 168.5 (s, CCMe$_3$), 46.6 (d, $^1J_{CH}$=122.3 Hz, CHMe$_2$), 39.4 (s, CMe$_3$), 31.0 (q,$^1J_{CH}$=116.1 Hz, CHMe$_2$), 26.3 (q,$^1J_{CH}$= 116.1 Hz, CMe$_3$).

EXAMPLE 4

(Li|Bu$^t$C(NCy)$_2$|)

A solution of 1,3-dicyclohexylcarbodiimide (5.00 g, 24.2 mmol) in Et$_2$O (50 mL) was cooled to 0° C. Bu$^t$Li (14.3 mL of a 1.7 M solution in pentane, 24.2 mmol) was added via syringe and the mixture was allowed to warm to room temperature. After 30 min the volatile components were removed under vacuum affording a yellow oily solid which was dried overnight under vacuum to yield a pale yellow powder. Trituration of this solid with pentane gave Li[Bu$^t$C (NCy)$_2$] as a pale yellow powder (4.91 g, 75%). $^1$H NMR (THF-d$_8$): δ 3.50 (m,2H,Cy), 1.81–0.93 (m,20H,Cy), 1.10 (s,9H,CMe$_3$). $^{13}$C NMR (THF-d$_8$): δ 168.3 (s,CCMe$_3$), 55.9 (d,$^1J_{CH}$=119.8 Hz, Cy-C$_1$), 39.5 (s,CMe$_3$), 37.7 (t,$^1J_{CH}$= 118.9 Hz,Cy), 31.1 (q,$^1J_{CH}$=117.7 Hz,CMe$_3$), 28.2 (t, partially obscured, Cy), 26.8 (t,$^1J_{CH}$=119.4 Hz, Cy).

EXAMPLE 5

({Bu$^t$C(NPr$^i$)$_2$}AlCl$_2$)

A solution of AlCl$_3$ (1.40 g, 10.5 mmol) in Et$_2$O (30 mL) was cooled to −78° C. and added dropwise to a slurry of Li|Bu$^t$C(NPr$^i$)$_2$| (2.00 g, 10.5 mmol) in Et$_2$O (50 mL) which was also at −78° C. The mixture was warmed to room temperature and stirred for 16 h, affording a slurry of a white solid in a yellow solution. The volatiles were removed under vacuum and the product was extracted from the LiCl with pentane. Concentration of the pentane extract and cooling to 0° C. afforded pure {Bu$^t$C(NPr$^i$)$_2$}AlCl$_2$ as opaque white crystals which were collected by filtration (2.01 g, 68%). $^1$H NMR (CD$_2$Cl$_2$): δ 4.12 (br sept, $^3J_{HH}$=5.9 Hz, 2H, CHMe$_2$), 1.43 (s,9H,CMe$_3$), 1.18 (d,$^3J_{HH}$=6.2 Hz, 12H, CHMe$_2$). $^{13}$C NMR (CD$_2$Cl$_2$): δ 184.3 (s, CCMe$_3$), 46.6 (d,$^1J_{CH}$=135.7 Hz, CHMe$_2$), 40.1 (s,CMe$_3$), 29.2 (q,$^1J_{CH}$=125.7 Hz, CMe$_3$), 25.9 (q,$^1J_{CH}$=124.1 Hz, CHMe$_2$). Anal. Calcd for C$_{11}$H$_{23}$N$_2$AlCl$_2$: C, 46.98; H, 8.24; N, 9.96. Found: C, 46.84; H, 8.12; N, 9.85. Mass Spec. (EI,m/z,$^{35}$Cl): 265 |M|$^+$.

EXAMPLE 6

({Bu$^t$C(NCY)$_2$}AlCl$_2$)

A solution of AlCl$_3$ (0.99 g, 7.4 mmol) in Et$_2$O (25 mL) was added dropwise to a slurry of Li|Bu$^t$C(NCy)$_2$|(2.00 g, 7.4 mmol) in Et$_2$O (50 mL) at −78° C. The mixture was warmed to room temperature and stirred for 18 h, affording a slurry of a white precipitate in a yellow solution. The volatiles were removed under vacuum and the product was extracted from the LiCl with toluene. Concentration of the toluene extract and cooling to 0° C. afforded pure {Bu$^t$ (NCy)$_2$}AlCl$_2$ as colorless crystals which were collected by filtration (1.84 g, 69%). $^1$H NMR (CD$_2$Cl$_2$): δ 3.62 (br m,2H,Cy), 1.41 (s,9H,CMe$_3$), 1.91 −1.71 (m,4H,Cy), 1.62 (m,2H,Cy), 1.30–1.09 (m,8H+2H,Cy). $^{13}$C NMR (CD$_2$Cl$_2$): δ 184.4 (s,CCMe$_3$), 54.6 (d,$^1J_{CH}$=138.7 Hz, Cy-C$_1$), 40.1 (s,CMe$_3$), 36.9 (t,$^1J_{CH}$=127.9 Hz,Cy), 29.3 (q,$^1J_{CH}$=127.7 Hz, CMe$_3$), 25.7 (t,$^1J_{CH}$=125.7 Hz,Cy), 25.6 (t,$^1J_{CH}$=125.7 Hz,Cy). Anal. Calcd for C$_{17}$H$_{31}$N$_2$AlCl$_2$: C, 56.51; H, 8.65; N, 7.75. Found: C, 56.22; H, 8.70; N, 7.67.

Mass Spec. (EI,m/z,$^{35}$Cl):360|M|$^+$.

EXAMPLE 7

({BU$^t$C(NPr$^i$)$_2$}AlMe$_2$)

A solution of AlMe$_2$Cl (0.25 mL, 2.7 mmol) in Et$_2$O (25 mL) was added dropwise to a slurry of Li|Bu$^t$C(NPr$^i$)$_2$|(0.50 g, 2.6 mmol) in Et$_2$O (30 mL) at −78° C. The reaction mixture was allowed to warm slowly to room temperature and was stirred for 18 h. The volatiles were removed under vacuum and the residue was extracted with pentane. The extract was evaporated to dryness under vacuum yielding {Bu$^t$C(NPr$^i$)$_2$}AlMe$_2$ as a pale yellow solid (0.57 g, 87%). $^1$H NMR (CD$_2$Cl$_2$): δ 4.07 (sept,$^3J_{HH}$=6.2 Hz,2H,CHMe$_2$), 1.38 (s,9H,CMe$_3$), 1.06 (d,$^3J_{HH}$=6.1 Hz,12H,CHMe$_2$), −0.81 (s,6H,AlMe$_2$). $^{13}$C NMR (CD$_2$Cl$_2$): 67 178.4 (s,CCMe$_3$), 45.8 (d,$^1J_{CH}$=135.3 Hz,CHMe$_2$), 40.0 (s,CMe$_3$), 29.7 (q,$^1J_{CH}$=127.0 Hz, CHMe$_2$), 26.3 (q,$^1J_{CH=}$125.5 Hz,CMe$_3$), −9.06 (br q,$^1J_{CH}$=117.7 Hz,AlMe$_2$). Anal. Calcd for C$_{13}$H$_{29}$N$_2$Al: C, 64.96; H, 12.16; N, 11.65. Found: C, 64.46; H, 11.90; N, 11.90. Mass Spec. (EI,m/z): 240 |M|$^+$, 225 |M —CH$_3$|$^+$.

EXAMPLE 8

({BU$^t$C(NCy)$_2$}AlMe$_2$)

A solution of AlMe$_2$Cl (0.71 mL, 7.7 mmol) in Et$_2$O (30 mL) was added dropwise to a slurry of Li|Bu$^t$C(NCy)$_2$| (2.00 g, 7.4 mmol) in Et$_2$O (40 mL) at −78° C. The mixture was allowed to warm to room temperature and was stirred for 15 h. The volatiles were removed under vacuum and the residue was extracted with pentane (3×15 mL). The extract was concentrated to 30 mL and maintained at room temperature affording {Bu$^t$C(NCy)$_2$}AlMe$_2$(2.00 g, 83%) as large colorless crystals which were collected by filtration.$^1$H NMR (CD$_2$Cl$_2$): δ 3.56 (m,2H,Cy), 1.80–1.69 (m,8H,Cy), 1.61–1.57 (m,2H,Cy), 1.36 (s,9H,CMe$_3$), 1.27–1.03 (m,8H+ 2H,Cy), −0.83 (s,6H,AlMe$_2$). $^{13}$C NMR (CD$_2$Cl$_2$): δ 178.5 (s,CCMe$_3$), 54.2 (d,$^1J_{CH}$=125.9 Hz, Cy-C$_1$), 39.9 (s,CMe$_3$), 37.3 (t,$^1J_{CH}$=119.3 Hz,Cy), 29.7 (q,$^1J_{CH}$=117.3 Hz,CMe$_3$), 26.1 (t,$^1J_{CH}$=119.3 Hz,Cy), 26.0 (t,$^1J_{CH}$=119.3 Hz, Cy), −9.1

(br q.$^1J_{CH}$=103.9 Hz.AlMe$_2$). Anal. Calcd for C$_{19}$H$_{37}$N$_2$Al: C. 71.20; H. 11.64; N. 8.74. Found: C. 71.18; H. 11.88; N. 8.73. Mass Spec. (EI.m/z): 320 |M|$^+$, 305 |M—CH$_3$|$^+$.

EXAMPLE 9

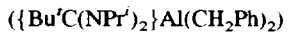

A solution of {Bu$^t$C(NPr$^i$)$_2$}AlCl$_2$ (0.50 g. 1.8 mmol) in Et$_2$O (25 mL) was cooled to −78° C. and PhCH$_2$MgCl (3.56 mL of a 1.0 M solution in Et$_2$O, 3.6 mmol) was added dropwise via syringe. The reaction mixture was allowed to warm to room temperature and was stirred for 15 h. The volatiles were removed under vacuum and the residue was extracted with pentane. The extract was evaporated to dryness under vacuum affording pure {Bu$^t$C(NPr$^i$)$_2$}Al(CH$_2$Ph)$_2$ as a viscous oil (0.55 g. 79%) that can be induced to solidify through storage at −40° C. $^1$H NMR (CD$_2$Cl$_2$): δ 7.11 (t.$^3J_{HH}$=7.6 Hz.4H.m-Ph), 7.02 (d.$^3J_{HH}$=6.9 Hz.4H.o-Ph), 6.88 (t.$^3J_{HH}$=7.3 Hz.2H.p-Ph), 4.00 (sept.$^3J_{HH}$=6.2 Hz.2H.CHMe$_2$), 1.75 (s.4H.CH$_2$Ph), 1.34 (s.9H.CMe$_3$), 0.94 (d.$^3J_{HH}$=6.2 Hz. 12H. CHMe$_2$). $^{13}$C NMR (CD$_2$Cl$_2$): δ 180.8 (s.CCMe$_3$), 146.8 (s.ipso-Ph), 128.2 (d.$^1J_{CH}$=155.8 Hz. o- or m-Ph), 127.5 (d.$^1J_{CH}$=149.4 Hz. o- or m-Ph), 121.7 (d.$^1J_{CH}$=148.5 Hz.p-Ph), 45.6 (d.$^1J_{CH}$=128.9 Hz.CHMe$_2$), 40.1 (s.CMe$_3$), 29.6 (q.$^1J_{CH}$=119.0 Hz.CMe$_3$), 26.3 (q.$^1J_{CH}$=116.4 Hz.CHMe$_2$), 21.4 (br t.$^1J_{CH}$=108.9 Hz. CH$_2$Ph). Anal. Calcd for C$_{25}$H$_{37}$N$_2$Al: C. 76.49; H. 9.50; N. 7.14. Found: C. 75.05; H. 9.63; N. 6.89. Mass Spec. (EI.mlz): 301 |M—CH$_2$Ph|$^+$.

EXAMPLE 10

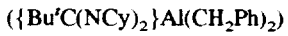

A solution of {Bu$^t$C(NCy)$_2$}AlCl$_2$(0.50 g. 1.4 mmol) in Et$_2$O (20 mL) was cooled to −78° C. and PhCH$_2$MgCl (2.76 mL of a 1.0 M solution in Et$_2$O, 2.8 mmol) was added dropwise by syringe. The mixture was allowed to warm slowly to room temperature and was stirred for 15 h. The volatiles were removed under vacuum and the residue was extracted with pentane. The extract was evaporated under vacuum affording pure {Bu$^t$C(NCy)$_2$}Al(CH$_2$Ph)$_2$ as a viscous white oil. (0.57 g. 87%). $^1$H NMR (CD$_2$Cl$_2$): δ 7.08 (t.$^3J_{HH}$=7.6 Hz.4H.m-Ph), 6.98 (d.$^3$JHH=6.9 Hz.4H.o-Ph), 6.84 (t.$^3$JHH=$^{7.3}$ Hz.2H.p-Ph), 3.44 (m.2H.Cy), 1.69 (s.4H. CH$_2$Ph), 1.63–1.51 (m.4H+2H.Cy), 1.27 (s.9H.CMe$_3$), 1.21-0.78 (m.14H.Cy). $^{13}$C NMR (CD$_2$Cl$_2$): 6 180.8 (s.CCMe$_3$), 146.9 (s.ipso-Ph), 126.2 (d.$^1J_{CH}$=155.8 Hz. o- or m-Ph), 127.5 (d.$^1J_{CH}$=147.6 Hz. o- or m-Ph), 121.6 (d.JCH= 151.$^3$ Hz.p-Ph), 54.0 (d. partially obscured. Cy-C$_1$), 40.0 (s.CMe$_3$), 37.1 (t.$^1J_{CH}$=117.7 Hz.Cy), 29.6 (q.$^1J_{CH}$=117.3 Hz.CHMe$_3$), 25.9 (t.$^1$JCH=118.2 Hz.Cy), 25.7 (t.$^1$JCH=$^{118.2}$ Hz.Cy), 21.4 (t.$^1J_{CH}$=108.7 Hz.CH$_2$Ph). Anal. Calcd for C$_{31}$H$_{45}$N$_2$Al: C. 78.77; H. 9.60; N. 5.93. Found: C. 78.62; H.9.58; N. 5.83.

EXAMPLE 11

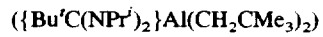

{Bu$^t$C(NPr$^i$)$_2$}AlCl$_2$ (0.50 g. 1.8 mmol) and LiCH$_2$CMe$_3$ (0.28 g. 3.6 mmol) were mixed as solids in the glove box. Et$_2$O (40 mL) was added at −78° C. and the mixture was allowed to warm slowly to room temperature, affording a colorless solution and a white precipitate. The mixture was stirred for 18 h and the volatiles were removed under vacuum. The residue was extracted with pentane (3×10 mL). The extract was taken to dryness under vacuum affording {Bu$^t$C(NiPr)$_2$}Al(CH$_2$CMe$_3$)$_2$ as a white solid (0.58 g. 93%). $^1$H NMR (CD$_2$Cl$_2$): δ 4.13 (sept.$^3J_{HH}$=6.2 Hz. CHMe$_2$), 1.39 (s.9H.CMe$_3$), 1.15 (d.$^3J_{HH}$=6.3 Hz. CHMe$_2$), 0.99 (s.18H.CH$_2$CMe$_3$), 0.27 (s.4H.CH$_2$CMe$_3$). $^{13}$C NMR (CD$_2$Cl$_2$): δ179.7 (s.CCMe$_3$), 46.1 (d.$^1J_{CH}$=121.0 Hz.CHMe$_2$), 40.1 (s.CMe$_3$), 35.2 (q.$^1J_{CH}$=112.2 Hz. CH$_2$CMe$_3$), 32.1 (br t. partially obscured. CH$_2$CMe$_3$), 31.6 (s. CH$_2$CMe$_3$), 29.8 (q.$^1J_{CH}$=121.2 Hz.CMe$_3$), 26.6 (q.$^1J_{CH}$=117.9 Hz. CHMe$_2$). Anal. Calcd for C$_{21}$H$_{45}$N$_2$Al: C. 71.54; H. 12.86; N. 7.95. Found: C. 70.46; H. 12.82; N. 7.72. Mass Spec. (EI.m/z): 281 |M—CH$_2$CMe$_3$|$^+$.

EXAMPLE 12

A solution of LiCH$_2$CMe$_3$ (0.43 g. 5.5 mmol) in Et$_2$O (20 mL) was added dropwise at −78° C. to an Et$_2$O solution (30 mL) of {Bu$^t$C(NCy)$_2$}AlCl$_2$ (1.00 g. 2.8 mmol). The reaction mixture was allowed to warm slowly to room temperature and was stirred for 15 h. The volatiles were removed under vacuum and the residue was extracted with pentane. The extract was evaporated to dryness under vacuum to afford pure {Bu$^t$C(NCy)$_2$}Al(CH$_2$CMe$_3$)$_2$ as a white solid material (1.13 g. 94%). $^1$H NMR (CD$_2$Cl$_2$): δ 3.63 (m.2H. Cy), 1.86–1.71 (m.8H.Cy), 1.60 (m.2H.Cy), 1.36 (s.9H. CMe$_3$), 1.30–1.09 (m.8H+2H.Cy), 0.99 (s.CH$_2$CMe$_3$), 0.25 (s.4H.CH$_2$CMe$_3$). $^{13}$C NMR (CD$_2$Cl$_2$): δ 179.7 (s.CCMe$_3$), 54.8 (d.$^1J_{CH}$=126.8 Hz. Cy-C$_i$), 40.0 (s.CMe$_3$), 37.2 (t.$^1J_{CH}$=124.3 Hz.Cy), 35.2 (q.$^1J_{CH}$=117.6 Hz. CH$_2$CMe$_3$), 32.1 (br t. partially obscured. CH$_2$CMe$_3$), 31.6 (s.CH$_2$CMe$_3$), 29.8 (q.$^1J_{CH}$=119.6 Hz. CMe$_3$), 26.2 (t$^1J_{CH}$=118.2 Hz. Cy), 26.1 (t.$^1J_{CH}$=118.2 Hz. Cy). Anal. Calcd for C$_{27}$H$_{53}$N$_2$Al: C. 74.95; H. 12.35; N. 6.47. Found: C. 73.87; H. 12.42; N. 6.60. Mass Spec. (EI.m/z): 362 |M—CH$_2$CMe$_3$|$^+$.

EXAMPLE 13

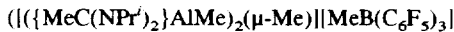

A solution of B(C$_6$F$_5$)$_3$ (0.77 g. 1.5 mmol) in CH$_2$Cl$_2$ (20 mL) was added to {MeC(NPr$^i$)$_2$}AlMe$_2$ (0.60 g. 3.0 mmol) also in CH$_2$Cl$_2$(15 mL). The reaction mixture was allowed to stir for 30 min at room temperature and the volatiles were removed under vacuum leaving an oily white solid. Trituration with pentane afforded |({MeC(NPr$^i$)$_2$}AlMe)$_2$(μ-Me) ||MeB(C$_6$F$_5$)$_3$| as a white powder (0.91 g. 83%). $^1$H NMR (CD$_2$Cl$_2$, 293 K): δ 3.79 (sept.$^3J_{HH}$=6.6 Hz.4H.CHMe$_2$), 2.31 (s.6H.CMe), 1.28 (d.$^3J_{HH}$=6.5 Hz.24H.CHMe$_2$), −0.38 (br s.9H.AlMe). $^1$H NMR (CD$_2$Cl$_2$, 193K): δ 3.79 (br sept.2H.CHMe$_2$), 3.67 (br sept.6H.CHMe$_2$), 2.33 (s.6H. CMe), 2.15 (s.6H.CMe), 1.30 (m.18H.CHMe$_2$), 1.18 (m.12H.CHMe$_2$), 1.02 (m.18H.CHMe$_2$), −0.17 (s. 6H. AlMe), −0.54 (s. 6H. Al-Me), −0.75 (s. 6H. AlMe). $^{11}$B NMR (CD$_2$Cl$_2$): δ −13.4 (br s. MeB(C$_6$F$_5$)$_3$). $^{13}$C NMR (CD$_2$Cl$_2$): δ 182.0 (s.CMe), 50.5 (d.$^1J_{CH}$=138.9 Hz. CHMe$_2$), 23.4 (q.$^1J_{CH}$=127.0 Hz. CHMe$_2$), 17.8 (q.$^1J_{CH}$=130.3 Hz. CMe), −5.6 (br q.$^1J_{CH}$=130.3 Hz. AlMe). Anal. Calcd for C$_{38}$H$_{46}$N$_4$Al$_2$BF$_{15}$: C. 50.23; H. 5.10; N. 6.17. Found: C. 50.46; H. 4.92; N. 6.09.

EXAMPLE 14

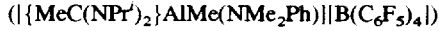

A CD$_2$Cl$_2$ solution (600 μL) of |HNMe$_2$Ph||B(C$_6$F$_5$)4| (85.3 mg. 0.11 mmol) was added to a vial containing {MeC(NPr$^i$)$_2$}AlMe$_2$ (21.1 mg. 0.11 mmol). The mixture was transferred to an NMR tube and NMR spectra were recorded showing complete conversion to [{MeC(NPr$^i$)$_2$}AlMe(NMe$_2$Ph)]|B(C$_6$F$_5$) 4]. $^1$H NMR (CD$_2$Cl$_2$: δ 7.63 (t.$^3$J$_{HH}$=7.9 Hz.2H.m-Ph). 7.51 (t.$^3$J$_{HH}$=7.3 Hz.1H.p-Ph). 7.47 (d.$^3$J$_{HH}$=7.9 Hz.2H.o-Ph). 3.58 (sept.$^3$J$_{HH}$=6.4 Hz. 2H.CHMe$_2$). 3.20 (s. 6H. NMe$_2$Ph). 2.17 (s. 3H. CMe). 1.03 (d.$^3$J$_{HH}$=6.5 Hz. 6H. CHMe$_2$). 0.92 (d.$^3$J$_{HH}$=6.4 Hz. 6H. CHMe$_2$). −0.30 (s. 3H. AlMe). $^{13}$C NMR (CD$_2$Cl$_2$): δ 182.0 (s.CMe). 143.7 (s. ipso-Ph). 131.4 (d.$^1$J$_{CH}$=159.4 Hz. o-Ph). 129.8 (d.$^1$J$_{CH}$=164.8 Hz. p-Ph). 120.9 (d.$^1$J$_{CH}$=153.1 Hz. m-Ph). 46.7 (q.$^1$J$_{CH}$=134.7 Hz. NMe$_2$). 46.0 (d.$^1$J$_{CH}$=125.2 Hz. CHMe$_2$). 24.7 (q.$^1$J$_{CH}$=119. Hz. CHMe$_2$). 24.6 (q.$^1$J$_{CH}$=119.7 Hz. CHMe$_2$). 12.7 (q.$^1$J$_{CH}$=122.6 Hz. CMe). −13.4 (br q.$^1$J$_{CH}$=116.8 Hz. ALMe).

EXAMPLE 15

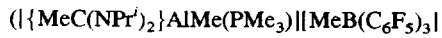

A CD$_2$Cl$_2$ solution of [({MeC(NPr$^i$)$_2$}AlMe)$_2$(µ-Me)]|MeB(C$_6$F$_5$)$_3$] was cooled in liquid N$_2$ and PMe$_3$ (5 equiv) was condensed onto the frozen solution. The mixture was warmed to room temperature and the $^1$H NMR spectrum was recorded. showing that complete formation of the trimethylphosphine adduct [{MeC(NPr$^i$)$_2$}AlMe(PMe$_3$)]|MeB(C$_6$F$_5$)$_3$] and {MeC(NPr$^i$)$_2$}AlMe$_2$ had occurred. To obtain a sample free from reaction byproducts. the NMR tube was evacuated and pumped on for 18 h. The resulting oily solid was redissolved in CD$_2$Cl$_2$ and the NMR spectra was recorded. and showed that only [{MeC(NPr$^i$)$_2$}AlMe(PMe$_3$)]|MeB(C$_6$F$_5$)$_3$] was present. $^1$H NMR (CD$_2$Cl$_2$): δ 3.62 (sept.$^3$J$_{HH}$=6.3 Hz. 2H. CHMe$_2$). 2.17 (s. 3H. CMe). 1.52 (d.$^2$J$_{PC}$=9.4 Hz. 9H. PMe$_3$). 1.10 (d.$^3$J$_{HH}$=6.3 Hz. 12H. CHMe$_2$). −0.27 (s. 3H. AlMe). $^{31}$p NMR (CD$_2$Cl$_2$): δ −34.55 (s.PMe$_3$). $^{13}$C NMR (CD$_2$Cl$_2$): δ 180.6 (s. CMe). 45.5 (d.$^1$J$_{CH}$=131.1 Hz. CHMe$_2$). 25.3 (q.$^1$J$_{CH}$=121.0 Hz. CHMe$_2$). 12.4 (q.$^1$J$_{CH}$=124.7 Hz. CMe). 9.1 (dq.$^1$J$_{PC}$=29.6 Hz.$^1$J$_{CH}$=127.6 Hz. PMe$_3$). −12.8 (br q.$^1$J$_{CH}$=109.6 Hz. AlMe).

EXAMPLE 16

([{MeC(NPr$^i$)$_2$}AlMe(PMe$_3$)]|B(C$_6$F$_5$)$_4$])

A CD$_2$Cl$_2$ solution of [{MeC(NPr$^i$)$_2$}AlMe(NMe$_2$Ph)]|B(C$_6$F$_5$)$_4$] was cooled in liquid N$_2$ and PMe$_3$ (5 equiv) was condensed onto the frozen solution. The mixture was warmed to room temperature and the $^1$H NMR spectrum was recorded. showing that formation of the trimethylphosphine adduct [{MeC(NPr$^i$)$_2$}AlMe(PMe$_3$)]|B(C$_6$F$_5$)4] and free NMe$_2$Ph had occurred. 1H NMR (CD$_2$Cl$_2$): δ 3.62 (sept. $^3$J$_{HH}$=6.3 Hz. 2H. CHMe$_2$). 2.17 (s. 3H. CMe). 1.52 (d. $^2$J$_{PC}$=9.4 Hz. 9H. PMe$_3$). 1.10 (d.$^3$J$_{HH}$=6.3 Hz. 12H. CHMe$_2$). −0.27 (s. 3H. AlMe). 31P NMR (CD$_2$Cl$_2$ δ −34.55 (s. PMe$_3$). $^{13}$C NMR (CD$_2$Cl$_2$): δ 180.6 (s. CMe). 45.5 (d.$^1$J$_{CH}$=131.1 Hz. CHMe$_2$). 25.3 (q.$^1$J$_{CH}$=121.0 Hz. CHMe$_2$). 12.4 (q.$^1$J$_{CH}$=124.7 Hz. CMe). 9.1 (dq.$^1$J$_{PC}$=29.6 Hz. $^1$J$_{CH}$ =127.6 Hz. PMe$_3$). −12.8 (br q.$^1$J$_{CH}$=109.6 Hz. AlMe).

Based upon the above synthesis illustration Examples 1–16. it can be seen that the cationic aluminum alkyl complexes are prepared by reacting a neutral precursor complex of the type R$^2$C(NR$^1$)(NR$^3$)AlX$_2$. where R$^1$, R$^2$, R$^3$ and X are as defined above. with an activator compound which is capable of abstracting one X− group from the precursor complex or of cleaving one Al—X bond of the precursor complex. Additionally. example 15 shows that the {MeC(NPr$^i$)$_2$}AlMe$_2$ moiety of [({MeC(NPr$^i$)$_2$}AlMe)$_2$(µ-Me]|MeB(C$_6$F$_5$) 3] can be displaced by the Lewis base PMe$_3$. and example 16 shows that the NMe$_2$Ph group of [{MeC(NPr$^i$)$_2$}AlMe(NMe$_2$Ph)]|B(C$_6$F$_5$)$_4$] can be displaced by PMe$_3$.

The following two additional examples illustrate the preparation of base-free cations.

EXAMPLE 17

A solution of {Bu$^t$C(NPr$^i$)$_2$}AlMe$_2$ (0.040 g. 0.17 mmol) in toluene (1.5 cm$^3$) was prepared in the dry box. This was added dropwise via pipette to a solution of 1 equiv B(C$_6$F$_5$)$_3$ (0.087 g. 0.17 mmol) also in toluene (2.5 cm$^3$) that was rapidly stirring in an ampoule fitted with a teflon tap. The ampoule was sealed and the mixture was removed from the dry box and stirred on a vacuum line for 30 mins. The volatiles were then removed under reduced pressure. leaving an off-white. oily residue. (CD$_2$Cl)$_2$ was added to this residue and the solution transferred to an NMR tube. The $^1$H NMR spectrum was recorded immediately and showed complete conversion to the desired base-free cation [{Bu$^t$C (NPr$^i$)$_2$}AlMe||MeB(C$_6$F$_5$)$_3$]. $^1$H NMR (CD$_2$Cl)$_2$: δ 4.12 (sept.$^3$J$_{HH}$=6.2 Hz. 2H. CHMe$_2$). 1.67 (br s. 3H. BCH$_3$). 1.42 (s. 9H. CMe$_3$). 1.09 (d.$^3$J$_{HH}$=6.2 Hz. CHMe$_2$). 0.96 (d.$^3$J$_{HH}$=6.2 Hz. CHMe$_2$). −0.44 (br s. 3H. AlMe). $^{13}$C NMR (CD$_2$Cl)$_2$: δ 181.3 (s. CCMe$_3$). 46.0 (d.$^1$J$_{CH}$=132.1 Hz. CHMe$_2$). 40.1 (s. CMe$_3$). 29.3 (q.$^1$J$_{CH}$=122.3 Hz. CMe$_3$). 26.4 (q.$^1$J$_{CH}$=125.3 Hz. CHMe$_2$). 25.5 (q.$^1$J$_{CH}$=121.2 Hz. CHMe$_2$). −8.7 (br q.$^1$J$_{CH}$=118.1 Hz. AlMe).

EXAMPLE 18

The product was prepared in an identical manner to that outlined above. using 0.033 g {Bu$^t$C(NCy)$_2$}AlMe$_2$ (0.10 mmol) and 0.053 g B(C$_6$F$_5$)$_3$ (1 equiv. 0.10 mmol). Again 100% conversion to the base-free cation was observed. $^1$H NMR (CD$_2$Cl)$_2$: δ 3.61 (m. 2H. Cy). 1.83–1.74 (br m. 4H. Cy). 1.66 (br s. 3H. BCH$_3$). 1.55 (br t. 4H. Cy). 1.37 (s. 9H. CMe$_3$). 1.25–0.98 (m. 8H. Cy). 0.89–0.79 (m. 4H. Cy). −0.46 (s. 3H. AlMe). $^{13}$C NMR (CD$_2$Cl)$_2$ δ 181.1 (s. CCMe$_3$). 54.1 (d.$^1$J$_{CH}$=134.0 Hz. Cy-C$_1$). 39.9 (s. CMe$_3$). 37.5 (t.$^1$J$_{CH}$=129.0 Hz. Cy). 36.6 (t.$^1$J$_{CH}$=126.2 Hz. Cy). 29.3 (q.$^1$J$_{CH}$=122.3 Hz. CMe$_3$). 25.8 (t.$^1$J$_{CH}$=122.5 Hz. Cy). −8.5 (q.$^1$J$_{CH}$=114.7 Hz. AlMe).

EXAMPLE 19

(Polymerization Procedure for Ethylene)

All polymerizations were carried out using transition metal-free conditions. employing glass apparatus and Teflon-coated stirrer bars. In a typical experiment. 0.02 g of {Bu$^t$C(NPr$^i$)$_2$}AlMe$_2$ was weighed out into a glass vial in the dry box. and 3 mL of dry toluene was added. 1 equiv of activator. based on the aluminum compound was weighed into a Fischer-Porter bottle and ca. 50 cm$^3$ of toluene was added. The aluminum complex solution was added dropwise over 2 minutes (using a pipette) to the rapidly stirring activator solution. ensuring efficient mixing of the 2 components. and a constant excess of activator (to limit formation of base adduct species). The apparatus was then removed from the dry box and connected to the polymerization equipment. consisting of an ethylene cylinder. metal vacuum line and gas purification system. This had been previously evacuated to remove any residual gas from the system. The mixture was allowed to equilibrate at the temperature required for the experiment (10–20 minutes) before the introduction of ethylene (Note, the Fischer-Porter bottle was placed under slight vacuum prior to introduction of the ethylene, to reduce the nitrogen content within and maximize ethylene dissolution in the solvent). The polymerization was typically allowed to run for 60 minutes, after which time the ethylene flow to the system was halted. The apparatus was vented in a fume hood and disassembled. 50–80 mL of a mixture of methanol (ca. 150 mL) and conc. HCl (ca. 1.5 mL) was added to the solution to quench the reaction and the precipitate (if any) was collected by filtration. The polymer was then washed with acidified water (ca. 1.5 mL conc. HCl in 100 mL $H_2O$) to ensure removal of the Al-salts, dried in a vacuum oven at 60° C. for 2–8 hours. The weight recorded and the activity calculated (see table).

The results of the ethylene polymerizations are arized in the table below.

Table of Results for Ethylene Polymerization
(neutral precursor complex = {Bu$^t$C (NPr$^i$)$_2$} AlMe$_2$,
ethylene pressure = 2 atm; solvent = toluene)

| Run | Activator Compound | Time (mins) | Temp (°C.) | Yield PE (g) | Activity (g PE/mol cat/hr/atm) |
|---|---|---|---|---|---|
| 1 | B(C$_6$F$_5$)$_3$ | 60 | 26 | 0.053 | 293 |
| 2 | B(C$_6$F$_5$)$_3$ | 60 | 60 | 0.115 | 697 |
| 3 | B(C$_6$F$_5$)$_3$ | 60 | 85 | 0.026 | 162 |
| 4 | [Ph$_3$C] [B(C$_6$F$_5$)$_4$] | 60 | 26 | 0.084 | 530 |
| 5 | [Ph$_3$C] [B(C$_6$F$_5$)$_4$] | 60 | 60 | 0.293 | 1177 |
| 6 | [Ph$_3$C] [B(C$_6$F$_5$)$_4$] | 30* | 60 | 0.266 | 3183 |
| 7 | [Ph$_3$C] [B(C$_6$F$_5$)$_4$] | 30* | 85 | 0.351 | 4145 |

(* = solution stopped stirring due to precipitate forming therefore stopped after 30 mins)

As can be seen from the above, effective catalysts for alpha-olefin polymerizations in particular are prepared that avoid any transition metals. It therefore can be seen that the invention accomplishes at least all of its stated objectives.

What is claimed is:

1. Aluminum amidinate compounds of the formula:

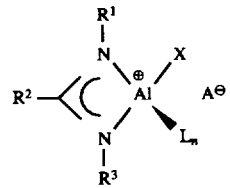

wherein $R^1$, $R^2$, and $R^3$ are selected from the group consisting of $C_1$ to $C_{50}$ alkyl, aryl and silyl groups, X is an anionic ligand, n=0 or 1, L, if present, is a labile Lewis-base or donor ligand, and $A^-$ is a counterbalancing non-coordinating or weakly coordinating anion.

2. A compound of claim 1 wherein $R^1$, $R^2$ and $R^3$ are selected from the group consisting of $C_1$ to $C_{12}$ alkyl, aryl and silyl groups.

3. A compound of claim 1 wherein X is hydride, dialkylamido, alkoxide, aryloxide, hydrocarbyl, halocarbyl, or thiolate.

4. A compound of claim 1 wherein L, if present, is selected from the group consisting of tetrahydrofuran, ethers, amines, alkylamines, pyridine and phosphines.

5. A compound of claim 1 wherein $A^-$ is a boron containing anion.

6. The process of synthesizing cationic aluminum compounds, comprising:
reacting a neutral precursor complex of the formula {$R^2C(NR^1)(NR^3)$}AlX$_2$ wherein $R^1$, $R^2$, and $R^3$ are selected from the group consisting of $C_1$ to $C_{50}$ alkyl, aryl, and silyl groups, with an activator compound that will either abstract an $X^-$ moiety from the precursor complex or cleave an Al—X bond.

7. The process of claim 6 wherein $R^1$, $R^2$, and $R^3$ are selected from the group consisting of $C_1$ to $C_{12}$ alkyl, aryl, and silyl groups.

8. The process of claim 6 wherein X is a hydride, dialkyl amido, alkoxide, aryloxide, hydrocarbyl, halo-carbyl or thiolate.

* * * * *

UNITED STATES PATENT AND TRADEMARK OFFICE
CERTIFICATE OF CORRECTION

| | | |
|---|---|---|
| PATENT NO. | : 5,777,120 | Page 1 of 1 |
| DATED | : July 7, 1998 | |
| INVENTOR(S) | : Richard F. Jordan and Martyn P. Coles | |

It is certified that error appears in the above-identified patent and that said Letters Patent is hereby corrected as shown below:

GRANT REFERENCE

Work for this invention was funded in part by a grant from National Science Foundation. Grant No. NSF CHE94-13022(003). The Government may have certain rights in this invention.

Signed and Sealed this

Fifth Day of March, 2002

Attest:

JAMES E. ROGAN
*Attesting Officer*     *Director of the United States Patent and Trademark Office*